United States Patent [19]

Healy et al.

[11] 4,031,155

[45] June 21, 1977

[54] DUAL DESORBENT COMPOSITION AND TEMPERATURE SEPARATION PROCESSES

[75] Inventors: Frank J. Healy, Morristown; Paul R. Geissler, Edison, both of N.J.

[73] Assignee: Exxon Research and Engineering Company, Linden, N.J.

[22] Filed: Mar. 26, 1976

[21] Appl. No.: 670,897

Related U.S. Application Data

[63] Continuation-in-part of Ser. No. 617,491, Sept. 29, 1975, abandoned, which is a continuation of Ser. No. 457,056, April 1, 1974, abandoned.

[52] U.S. Cl. .................... 260/674 SA; 208/310 Z; 210/31 C
[51] Int. Cl.² ............... C10G 25/04; B01D 15/08; C07C 7/13
[58] Field of Search .......... 260/694 SA; 208/310 Z; 210/31 C

[56] References Cited

UNITED STATES PATENTS

| | | | |
|---|---|---|---|
| 3,201,491 | 8/1965 | Stine et al. | 260/674 SA |
| 3,455,815 | 7/1969 | Fickel | 208/310 |
| 3,696,107 | 10/1972 | Neuzil | 260/674 SA |
| 3,715,409 | 2/1973 | Broughton | 260/674 SA |
| 3,732,325 | 5/1973 | Pharis et al. | 260/674 SA |
| 3,761,533 | 9/1973 | Otani et al. | 260/674 SA |
| 3,843,518 | 10/1974 | Magee et al. | 210/31 C |
| 3,894,109 | 7/1975 | Rosback | 260/674 SA |

*Primary Examiner*—Delbert E. Gantz
*Assistant Examiner*—G. E. Schmitkons
*Attorney, Agent, or Firm*—C. Leon Kim

[57] ABSTRACT

Dual desorbent composition and dual temperature techniques are provided as improvements for a simulated moving bed adsorption-desorption separation process which help reduce total desorbent requirements. The invention describes a process for continuously separating, in a liquid phase, components of a $C_8$ aromatic feed mixture by contacting said feed mixture with a solid sorbent and utilizing a simulated countercurrent flow system wherein a liquid stream flows through serially and circularly interconnected desorption, rectification and sorption zones. One of the embodiments envisioned in the present improved process is directed to the employment of two desorbent streams of different strengths. This embodiment minimizes total amount of desorbent requirements by using a strong desorbent stream in the desorption zone and a suitable weaker desorbent stream in the rectification zone to achieve the desired separation. In another embodiment, the concept of temperature gradient is utilized to increase the desorbing power of the desorbent employed. Such an embodiment is carried out by providing a means of heating the desorbent stream prior to its introduction to the desorption zone and thereafter removing any residual heat before the desorbent stream passes to the rectification zone by means of a heat exchanger. Further, both the dual desorbent composition and the dual temperature techniques can be also simultaneously employed as another embodiment.

21 Claims, 3 Drawing Figures

DUAL DESORBENT COMPOSITION

DUAL TEMPERATURE

DUAL TEMPERATURE-COMPOSITION

DUAL DESORBENT COMPOSITION AND TEMPERATURE SEPARATION PROCESSES

CROSS-REFERENCE TO RELATED APPLICATIONS

This application is a continuation-in-part of pending U.S. Ser. No. 617,491, filed Sept. 29, 1975, which is in turn a continuation of U.S. Ser. No. 457,056, filed Apr. 1, 1974 both now abandoned.

BACKGROUND OF THE INVENTION

This invention relates to improvements for a separation process which utilizes a simulated countercurrent flow system wherein a fluid stream flows through serially and circularly interconnected desorption, rectification and sorption zones. More particularly, the improvements concern the use of a dual desorbent composition technique carried out by means of the introduction of two different desorbent streams which minimizes the total amount of desorbent requirements. Additionally in another embodiment, the improved process includes a temperature gradient technique to increase the strength of the desorbent stream employed whereby the desorbent stream is first heated prior to its introduction to the desorption zone with a heat exchanger thereby increasing its desorbent strength and reducing overall desorbent requirements.

The present process employing the above embodiments is an improvement of the simulated countercurrent flow processes described in U.S. Pat. No. 3,761,533 and U.S. Pat. No. 3,201,491. It is known that adsorption-separation processes of liquid feed mixtures, the technique of employing a moving bed type adsorption process wherein said moving bed comprises sorbent particles which are countercurrently contacted with streams of liquid feedstock and desorbent, results in a high degree of purity for the adsorbed product. This process and the so-called simulated countercurrent flow system wherein the solid sorbent particles are stationary have been proposed and disclosed in the above-referred to patents.

In the latter known process, an adsorption separation column is divided into three (or four equivalent) zones: a sorption zone, (a primary rectification zone), a desorption zone and a (secondary) rectification zone. A downstream portion of the sorption zone is also called a primary rectification zone. These zones are serially interconnected in order and a continuously circulated fluid stream flowing through the three (or four) zones is maintained by circulating the effluent fluid from an outlet of the last zone to an inlet of the first zone; all the points of introducing and withdrawing the inlet and outlet streams are simultaneously shifted, at stated intervals of time, in a downstream direction to provide thereby a simulated countercurrent flow system wherein there is achieved a processing effect similar to that observed in the moving-bed type adsorption process. This process for a simulated countercurrent flow system in an adsorption-separation process may be described as follows. In such a process, at least one of the components of the liquid feed mixture is selectively sorbed by contact with solid sorbent particles; said liquid feed mixture is allowed to flow through three serially and circularly interconnected zones: a desorption zone, a rectification zone and a sorption zone, each zone being divided into a plurality of serially interconnected sections, each section being packed with a mass of solid sorbent particles; introducing a desorbent stream into the first section of the desorption zone; introducing the liquid feed mixture to the first section of the sorption zone and withdrawing a raffinate effluent comprising a less sorbed component and the desorbent from the sorption zone; and all the points of introducing and withdrawing the liquid steams into and from the sections are simultaneously shifted, at stated intervals of time, in a downstream direction, while maintaining the same order of continuity and the same spatial relationship between all the points.

In conducting the above-described process, several attempts were made to reduce the total desorbent requirements and also enhance the purity of the recovered sorbate. Stine et al., for example, disclosed a process in U.S. Pat. No. 3,201,491 (1965) which employs a portion of the desorption effluent withdrawn from the last section of the desorption zone by passing it directly into the (secondary) rectification zone in order to physically wash the raffinate materials remaining in the inactive void interstices between the active sorbent particles. An externally-prepared purging fluid comprising the sorbate and raffinate components of the feedstock was also claimed in their patent. Another improvement described in U.S. Pat. No. 3,455,815 (Fickel; 1967) envisions the employment of a stream consisting essentially of an inert material in order to flush non-selectively sorbable components of the feedstock from the interstitial void spaces between the sorbent particles in the rectification zone. A third method which is described in U.S. Pat. No. 3,761,533 (Otani et al.; 1973) introduces a portion of the desorption effluent which is rich in sorbate content into the rectification zone for the purpose of enhancing the purity of the sorbate component adsorbed within the rectification zone.

The above methods, however, contain certain deficiencies. The use of a portion of the desorption effluent will not only result in an increase in the desorbent consumption but also can desorb certain amount of sorbate adsorbed within the rectification zone and thereby limit the overall efficiency of the system. Further, Fickel's concept of employing a flushing stream consisting essentially of an inert material may not provide an adequate means to desorb chemically-adsorbed raffinate materials; and, consequently, the purity of the sorbate product may not be satisfactory. It has now been discovered that the employment of the dual desorbent composition technique and/or the dual temperature technique described herein can substantially eliminate the above deficiencies and markedly improve the overall performance of sorption-separation processes.

SUMMARY OF THE INVENTION

In accordance with the present invention, simulated countercurrent flow adsorption-separation processes as described above are operated with the dual desorbent composition technique of the instant invention. In this inventive embodiment, two desorbent streams of different strengths are employed. The first desorbent stream, $D_1$, when employed in the desorption zone, is more strongly sorbable on the sorbent particles than the most strongly sorbable component of the feed stream, while the second desorbent stream, $D_2$, which is introduced into the rectification zone, is less sorbable than $D_1$ and is preferentially intermediate in strength between the most strongly adsorbed sorbate and the weakly adsorbed raffinate. $D_2$ may consist of the same desorbent material as $D_1$ but is made less strongly adsorbable by dilution with an inert material such as paraffin. The amount of the inert material employed in $D_2$ should not be higher than 90 weight percent of $D_2$.

In another separate embodiment of the present invention, the simulated countercurrent separation processes can be also improved by the use of a temperature gradient technique. It has been discovered that, by preheating the desorbent stream to higher temperatures prior to its introduction to the desorption zone with a heat exchanger or some other means, the desorbing strength of the desorbent stream is significantly increased. In this embodiment, therefore, higher temperatures in the desorption zone permit the use of smaller amounts of desorbent than would be required at lower temperatures. Simultaneously, in accordance with this embodiment, lower temperatures are employed in the rectification and the sorption zones to permit easy adsorption of the feed. In practicing this inventive embodiment, there should be maintained a minimum temperature difference of about 15° C. between the heated desorbent stream and the operating temperatures of the rectification and the sorption zones.

In a further embodiment, the simulated countercurrent flow separation process may be operated by combining both the dual desorbent composition and the dual temperature techniques. This embodiment utilizes a weaker desorbent $D_2$ in the rectification zone and a stronger desorbent $D_1$ in the desorption zone, with $D_1$ being at a higher temperature than $D_2$. The result of the combination would be a much greater saving in the desorbent requirements and in many cases result in greater reduction in cost than either of the embodiments effected separately.

In a preferred embodiment, the improved process is applicable to the separation of paraxylene or paraxylene and ethylbenzene from $C_8$ isomer feedstreams. The separation of these isomers from a $C_8$ aromatic isomer feedstream which may comprise ethylbenzene, paraxylene, orthoxylene and metaxylene may be carried out by utilizing particular crystalline metal aluminosilicate sorbent materials. Examples of crystalline metal aluminosilicate sorbents useful for the separation of xylene isomers by means of the present process include potassium substituted zeolite X or Y, barium substituted zeolite X or Y, barium and potassium substituted X or Y. Other useful crystalline metal aluminosilicate sorbents that may be employed in the present invention can be found described in copending application Ser. No. 282,983, filed Aug. 23, 1972 and U.S. Pat. Nos. 3,732,325 and 3,734,974.

In this specification, carrier fluid or inert material is taken as liquid materials which are not significantly adsorbed by the sorbent substrate in the presence of feed mixture components. Eluent or desorbent is a term to describe liquid materials which are adsorbed by the substrate and compete for adsorption sites with the feed components.

The desorbent described above is generally a material capable of displacing sorbate components of the feedstock already adsorbed on the solid sorbent when the beds now comprising the desorption zone were in the rectification zone of a previous cycle of operation. The stream flowing through the successive beds of the desorption zone thus comprises a mixture of desorbent and desorbed sorbate released from an upstream bed of sorbent. Suitable desorbents useful in the present $C_8$ aromatic isomer separation process include toluene, m-diisopropylbenzene (m-DIPB), p-diethylbenzene (p-DEB), mixtures of diethylbenzene isomers (DEB), o-dichlorobenzene (o-DCB) and the like. While two different desorbent materials may be employed to prepare the stronger desorbent stream $D_1$, e.g., o-dichlorobenzene, and the weaker desorbent stream $D_2$, e.g., m-DIPB, it may be preferable to utilize one desorbent material admixed with different amounts of an inert material. Paraffinic materials having from 8 to 16 carbon atoms may be employed as the inert desorbent diluent. The stronger desorbent stream $D_1$ may be prepared by admixing, with an inert diluent, one of the desorbent materials enumerated above in an amount ranging from about 40 to about 100 wt. %, preferably from about 50 to about 95 wt. %, and more preferably from about 60 to about 85 wt. % based on the total amount of the desorbent mixture. Similarly, the weaker desorbent stream $D_2$ may comprise one of said desorbent materials in an amount within the range of from about 10 to about 60 weight percent, preferably from about 15 to about 50 weight percent, and more preferably from about 20 to about 35 weight percent based on the total mixture of the desorbent material and an inert diluent. The concentration of the desorbent material present in $D_1$ should be higher than that of the desorbent material present in $D_2$ at least by 20 wt.%. The volume ratio of the stronger desorbent stream $D_1$ to the weaker desorbent stream $D_2$ is in the range of from about 4/1 to about 1/3, preferably from about 3/1 to about 1/2, and more preferably from about 2/1 to about 1/1.

In applying the present invention to a commercial sorption-desorption system for separating $C_8$ aromatic isomers, the operating temperatures may vary from case to case. In general, however, the operable temperatures are in the range of from about 25° to about 200° C., preferably from about 75° to about 160° C., and more preferably from about 90° to about 145° C. When the dual temperature technique with a single desorbent stream is employed, the minimum temperature difference between the temperature of the desorbent stream introduced into the desorption zone and that of the streams flowing into the rectification and the sorption zones should be at least about 15° C. The upper limit of the temperature difference is normally controlled by the critical temperature at which paraxylene begins to isomerize, i.e., about 200° C.

When this dual temperature technique with a single desorbent stream is employed, the desorbent stream may comprise one of the suitable desorbent materials enumerated above in an amount within the range of from about 15 to about 100 weight percent, preferably from about 20 to about 80 weight percent, and more preferably from about 25 to about 67 weight percent and the corresponding amount of an inert material, e.g., $C_8$ to $C_{16}$ paraffinic materials.

DESCRIPTION OF THE PREFERRED EMBODIMENTS

Figure 1:
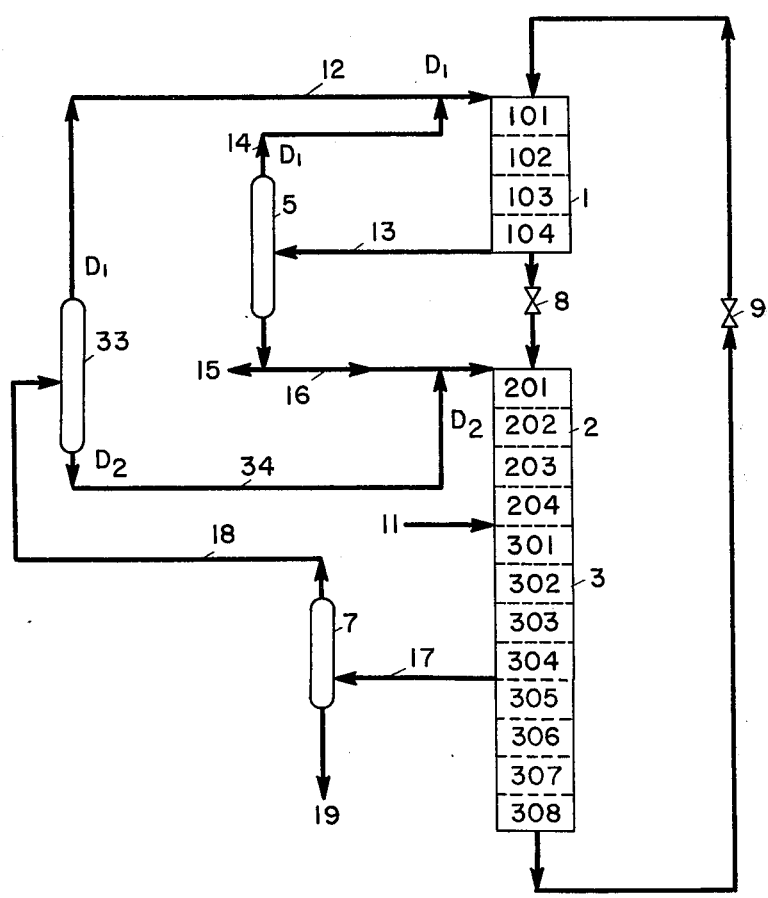
FIG. 1 represents a simplified version of a simulated moving-bed countercurrent separation system which employs two desorbent streams of different strengths: the stronger desorbent stream in the desorption zone and the weaker desorbent stream in the rectification zone.
Figure 2:
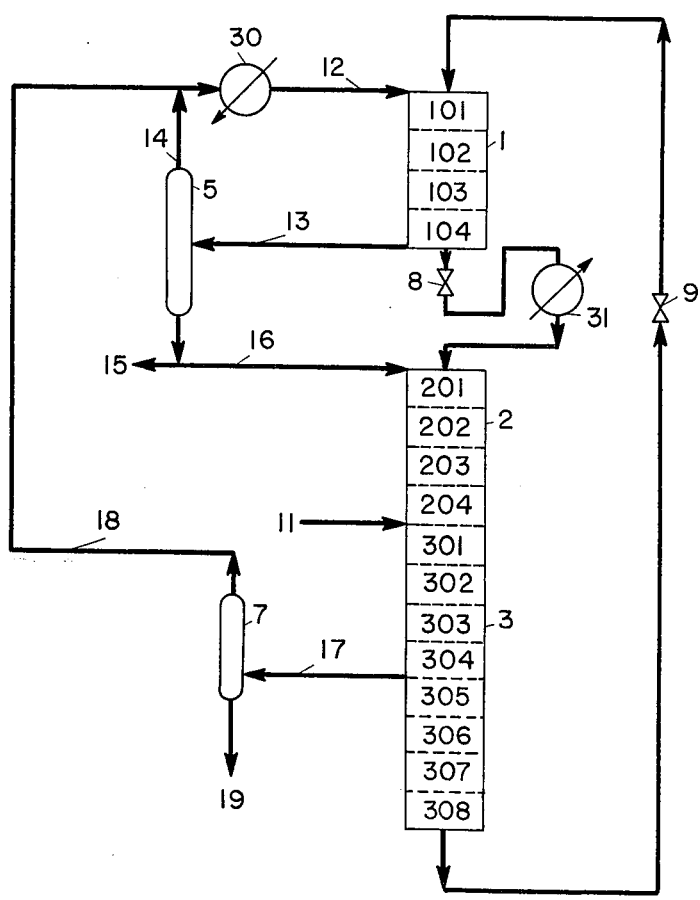
FIG. 2 shows a simulated moving-bed system which employs the desorbent stream with higher temperature in the desorption zone.
Figure 3:
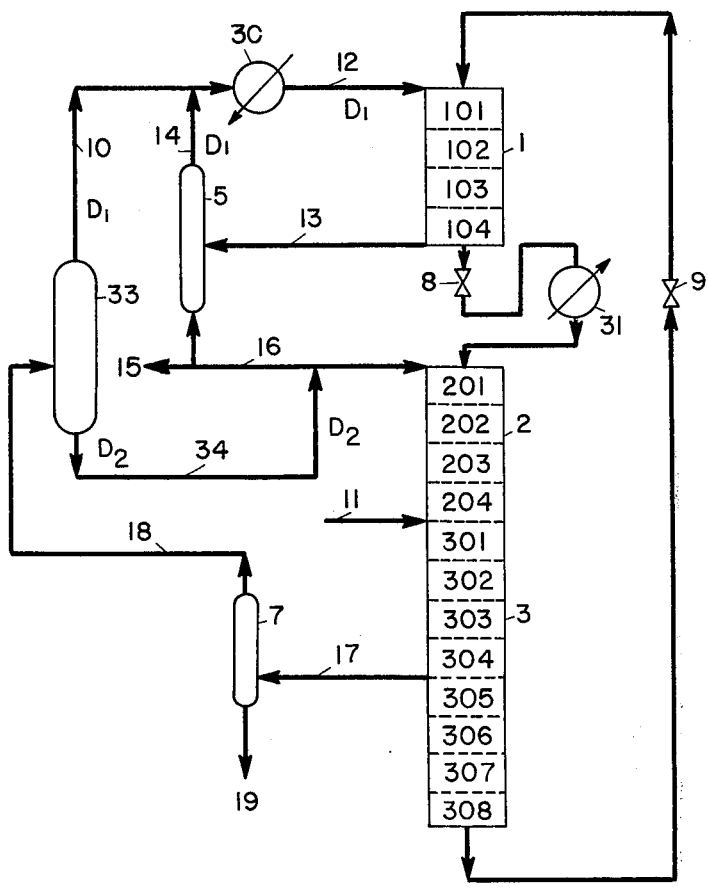
FIG. 3 illustrates a simulated moving-bed system which combines the dual desorbent composition and the dual temperature techniques in order to markedly enhance the separation efficiency of the sytem.

This instant invention and its embodiments will be further understood by reference to FIGS. 1, 2 and 3. The simulated moving-bed sorption-desorption systems illustrated in these figures are assumed to be under their steady-state operating conditions; and, consequently, it is assumed that no fresh feeds of the desorbent materials need be added as the desorbent streams with chosen concentrations will be constantly regenerated and recycled within the sytems. As shown in FIG. 1, the stronger desorbent stream $D_1$ flows into the first section 101 of the desorption zone 1 through line 12 which is joined by line 14. It should be noted that this desorption zone, in the previous cycle of operation, functioned as the rectification zone 2; and that only the desired sorbate components(s), e.g., paraxylene or paraxylene and ethylbenzene, has been selectively retained and sorbed onto the solid sorbent particles charged in the desorption zone. This selectively retained sorbate is desorbed by the stronger desorbent stream 12 within the desorption zone 1; and the mixture comprising the eluted sorbate and the desorbent, which mixture will be called the desorption effluent, is withdrawn through an outlet of the last section 104 of the desorption zone 1. All or a major portion of this desorption effluent is then sent through line 13 to a distillation column 5 where the desorption effluent is separated into the desorbent stream 14 which is recycled to the desorption zone and the sorbate-product stream. All or a major portion of the sorbate product is withdrawn from the system as the final product 15; and the remaining minor portion 16 may be optionally sent to the top section 201 of the rectification zone 2 as a reflux stream. A minor portion of the desorption effluent may also be optionally routed to the rectification zone 2 through a valve 8. The weaker desorbent stream $D_2$ which is reconstituted in distillation column 33 is introduced, through line 34 joining line 16, into the top section 201 of the rectification zone 2 in order to effect the desorption of certain weakly-sorbed raffinates, e.g., metaxylene, orthoxylene and possibly ethylbenzene, so that, when this rectification zone becomes a desorption zone in the further cycle of operation, only those desired sorbate component(s), e.g., paraxylene or paraxylene and ethylbenzene, may remain adsorbed on the sorbent substrate in a quality of high purity. A liquid feed mixture 11 comprising at least two sorbable $C_8$ aromatic isomers such as paraxylene, ethylbenzene, orthoxylene and metaxylene is injected into the top section 301 of the sorption zone 3. In the sorption zone 3, the feed flow joined by the effluent from the rectification zone (not shown) is countercurrently contacted with the simulated upward flow of the solid sorbent particles, resulting in the adsorption of the sorbable components of the feedstream onto the sorbent particles. The mixture of the desorbent and less sorbable raffinate materials which have lost sorption sites to more strongly sorbed molecules is then withdrawn from an outlet point positioned between sections 304 and 305 of the sorption zone 3 through line 17. The raffinate effluent is then sent to distillation column 7 wherein the raffinate effluent is separated into the desorbent stream 18 and the raffinate product 19.

In typical operations, the entire liquid stream flowing through the sorption zone 3 is divided into two portions: one portion being withdrawn from zone 3 as a raffinate effluent 17 and the other portion being allowed to flow directly down into the remaining sections 305, 306, 307, 308. These remaining sections are sometimes called a primary rectification zone. The number of the sections existing downstream from the withdrawal point of raffinate effluent 17 in the sorption zone 3 is determined in such a manner that the concentration of the raffinates contained in the stream flowing down through these sections reaches approximately zero at the bottom of the last section 308. Thus, the stream substantially free of raffinate components is directly and continuously introduced through a valve 9 into the desorption zone.

The sorption zone 3 may also be operated without the downstream sections 305, 306, 309 and 308. In this embodiment of operation, all or a major portion of the raffinate effluent 17 is withdrawn from the last section 304 of the sorption zone; and a minor portion of the raffinate effluent may be optionally routed, through valve 9, into the top section 101 of the desorption zone 1.

In general, the desorbent stream 18 recovered from distillation column 1 has a higher concentration than that of $D_2$, due to the influx of, in addition to the weaker desorbent stream $D_2$, an optional amount of the stronger desorbent stream $D_1$ from the desorption zone 1 through valve 8 into the rectification and the sorption zones 2,3 and also due to the presence of the strong desorbent material desorbed from the sorbent particles charged within the sorption zone 3. This strong desorbent material eluted in the sorption zone 3 is the fraction which has stayed adsorbed onto the sorbent substrate from the previous cycle when the sorption zone 3 functioned as the desorption zone 1. In order to reconstitute the weaker desorbent stream $D_2$, therefore, the desorbent stream 18 from distillation column 7 is further treated in distillation column 33. If two different desorbing materials or eluents are employed, the eluent with stronger desorbing ability can be recovered, for example, as the tops product and the weaker desorbing material as the bottoms product. If an identical desorbent material and a common diluent are used, the concentrations of the inert material in the bottoms and the tops product streams can be controlled so as to obtain the two $D_1$ and $D_2$ streams with their desired strengths.

The dual temperature embodiment may be more readily understood with reference to FIG. 2 which shows the desorbent stream being heated prior to its introduction to desorption zone 1 with a heat exchanger 30 or by other suitable means known in the art; and removing the residual heat, through the use of heat exchanger 31, before a portion of the desorption effluent passes into the rectification zone. Normally, the separation system is operated isothermally (except the desorption zone in this embodiment); and the temperature difference between the heated desorbent stream 12 and other streams going into the rectification zone should be maintained at least at about 15° C. It should be understood that the temperature of the reflux stream 16 has been adjusted, through the use of suitable means, e.g., a heat exchanger (not shown), so that the rectification zone can be maintained at a substantially isothermal condition. Flow sequence in FIG. 2 is otherwise identical to that described above for FIG. 1, except that distillation column 33 and associated stream 34 have been deleted.

Other applicable schemes for this embodiment include the utilization of distillation columns 5 and 7 in such a way to produce stream 12 at a sufficiently high temperature; and also heating of the desorption zone by means of a heating medium other than the desorbent stream, e.g., electric heating tapes, thereby eliminating the need for employing heat exchanger 30. Additionally, heat exchanger 31 may be eliminated if the heat capacity of desorption zone 1 is large enough to adequately cool the desorption effluent, a portion of which passing through valve 8.

The embodiment which combines both the dual temperature and the dual composition concepts may be more readily understood with reference to FIG. 3 which shows the strong desorbent stream (stream 10 from distillation column 33 and stream 14 from distillation column 5) being heated prior to its introduction to desorption zone 1 with a heat exchanger 30. Weak desorbent stream 34 flows into the first section 201 of the rectification zone 2, along with an optional amount of reflux stream 16. Stream 34 is weaker in desorbability than stream 12 by virtue of both its lower temperature and its lower concentration of eluent in its eluent-carrier or desorbent-diluent composition. Again, the temperatures of all the streams flowing into and leaving from the system, except the desorption zone in this embodiment, are assumed to be maintained substantially identical through the use of suitable means, e.g., a heat exchanger (not shown in FIG. 3), known in the art. Although it is not always necessary to maintain a minimum temperature difference between streams 12 and 34 in this embodiment, a higher temperature gradient is more desirable as it entails a higher efficiency. A minor portion of the desorption effluent from the last section 104 of the desorption zone may be optionally sent to the rectification zone after its temperature is adjusted to a temperature compatible to that of the rectification zone through the use of heat exchanger 31. Flow sequence in FIG. 3 is otherwise identical to that described above for FIG. 1.

The process of the present invention is further illustrated by the following examples.

EXAMPLE 1

Potassium Y sieve was ground to 20–40 mesh and about 30 grams were loaded into a 9-foot long, 0.25 inch O.D., 0.18 inch I.D. stainless steel column. A carrier-eluent mixture of 25% metadiisopropylbenzene (m-DIPB) and 75% n-$C_{12}$ paraffin was fed through the column at 130° C. and at a constant flow rate of 1.5 cc per minute. The carrier-eluent flow was stopped and a 2.0 cc sample of 20% paraxylene, 20% ethylbenzene, 20% orthoxylene and 40% metaxylene was injected into the stream upstream of the packed column through a sixport sample loop valve. Carrier-eluent flow was restarted immediately and samples of the stream eluting from the end of the column were taken periodically. Each sample was analyzed for the weight percentage of the $C_8$ aromatics by gas chromatography. The results show that all of the paraxylene injected was eluted from the column within a total elution-mixture volume of 100 cc.

EXAMPLES 2 THROUGH 20

The procedure of Example 1 was repeated with various sieves, carrier-eluent mixtures, and temperatures as specified in Table I in order to demonstrate that higher concentrations and/or higher temperatures of a desorbent stream can result in the desorption of the most selectively sorbed sorbate, e.g., paraxylene, with lesser amounts of desorbent. However, it can be also noted, from the last column of Table I, that such reductions in the desorbent consumption do not necessarily enhance the purity of the recover sorbate.

TABLE I

| Example | Sieve | Desorbent[1] | Column Temp., ° C. | Total Elution Volume for Complete Elution of Paraxylene, cc. | Fraction of Paraxylene Eluted Free of Other Isomers, % (4) |
|---|---|---|---|---|---|
| 1 | KY | 25% MDIPB | 130 | 100 | 95 |
| 2 | " | 25% MDIPB | 160 | 92 | 51 |
| 3 | " | 90% MDIPB | 130 | 57 | 62 |
| 4 | " | 90% MDIPB | 160 | 39 | 29 |
| 5 | " | 25% ODCB[2] | 100 | 78 | 30 |
| 6 | " | 25% ODCB[2] | 130 | 65 | 20 |
| 7 | " | 10% ODCB[2] | 130 | 156 | 80 |
| 8 | " | 17.5% ODCB[2] | 130 | 101 | 50 |
| 9 | " | 25% ODCB[2] | 130 | 65 | 20 |
| 10 | " | 32.5% ODCB[2] | 130 | 60 | 14 |
| 11 | " | 50% ODCB[2] | 130 | 35 | 5 |
| 12 | BaKY | 25% ODCB[2] | 100 | >225 | 60 |
| 13 | " | 50% ODCB[2] | 100 | 177 | 35 |
| 14 | " | 100% ODCB[2] | 100 | 103 | 5 |
| 15 | K(st)NH$_4$Y[3] | 25% ODCB | 75 | 155 | 55 |
| 16 | " | 25% ODCB | 130 | 111 | 20 |
| 17 | BaKY | 25% Toluene | 100 | 84 | 60 |
| 18 | " | 40% Toluene | 100 | 60 | 35 |
| 19 | " | 50% Toluene | 100 | 50 | 20 |
| 20 | " | 100% Toluene | 100 | 38 | 10 |

[1] Remaining portions of desorbent were comprised of n-$C_{12}$ paraffin.
[2] ODCB - orthodichlorobenzene.
[3] K(st)NH$_4$Y is potassium exchanged steamed ammonium Y zeolite.
[4] The data in this last column for Examples 1 to 5 were actually measured; and the data for Examples 6 to 20 were estimated.

EXAMPLE 21

Example 21 is designed to illustrate that, by employing two desorbent streams, $D_1$ and $D_2$, one can obtain both high elution efficiency and high separability of the desired sorbate(s), e.g., paraxylene, from other $C_8$ aromatic isomers.

The process as shown in FIG. 1 utilizing distillation column 33 to supply a strong desorbent stream 12 comprised of about 90% m-DIPB and about 10% n-$C_{12}$ paraffin and a weak desorbent stream 34 comprised of about 25% m-DIPB and about 75% n-$C_{12}$ paraffin was simulated by employing the elution column described in Example 1 charged with BaKy sieve at a temperature of about 130° C. When a feed mixture stream 11 composed of approximately 20% ethylbenzene, 20% paraxylene, 40% metaxylene, and 20% orthoxylene was used in the process, the volume ratio of desorbent stream 14 to product paraxylene 15 was found to be 6. The amount of paraxylene eluted free of other isomers was about 95% of the total amount of paraxylene in the feed; and the volume ratio of $D_1$ (stream 12) to $D_2$ (stream 34) was about 3.

EXAMPLE 22

The process as shown in FIG. 2 utilizing a heater 30 to preheat desorbent stream 12 composed of approximately 25% m-DIPB and 75% n-$C_{12}$ paraffin to about 160° C. was simulated by employing the same elution column charged wit BaKY sieve at a temperature of about 130° C. and the same feed mixture as in Example 21. The volume ratio of desorbent stream 14 to product paraxylene 15 was 9; and the amount of paraxylene eluted free of other isomers was about 95% based on the total paraxylene fed. The volume ratio of the heated desorbent stream 12 to the cooled stream passing the heat exchanger 31 was about 4.

EXAMPLE 23

The process as shown in FIG. 3 utilizing distillation column 33 and preheater 30 to supply a high temperature desorbent stream 12 containing approximately 90% m-DIPB and 10% n-$C_{12}$ paraffin at about 160° C. and a weak desorbent stream 34 composed of approximately 25% m-DIPB and 75% $C_{12}$ paraffin at about 130° C. was simulated by employing the same elution column and the same feed mixture as in Example 21. The volume ratio of desorbent stream 14 to product paraxylene 15 was found to be 4; and the amount of pure paraxylene eluted was about 95% of the total paraxylene fed. The volume ratio of $D_1$ (stream 12) to $D_2$ (stream 34) was about 2.

EXAMPLE 24

The procedure of Example 22 was repeated except that desorbent stream 12 was not heated and was at the same temperature (130° C.) as desorbent stream 34. It was found that the volume ratio of desorbent stream 14 to product paraxylene 15 was 10.

Examples 21 through 24 show that the use of a stronger desorbent in desorption zone 1, wherein its strength is increased by either an increase in temperature and/or an increase in eluent concentration, decreases the overall desorbent volume requirements and also enhances the separation efficiency of pure paraxylene.

EXAMPLES 25 THROUGH 28

Examples 25–28 are designed to show that the concentration of a desorbing material contained in the weaker desorbent stream $D_2$ should be at least higher than about 10 weight percent based on the total desorbent mixture to effect a recovery of substantially pure paraxylene.

The procedure of Example 1 was repeated with varying compositions of the initial eluent-carrier stream, i.e., 5% toluene/95% n-$C_{12}$ (Example 25), 10% toluene/95% n-$C_{12}$ (Example 26), 15% toluene/85% n-$C_{12}$ (Example 27), and 20% toluene/80% n-$C_{12}$ (Example 28), which initial compositions were then raised to 60% toluene/40% n-$C_{12}$ after the elapse of the times noted in Table II. Samples were taken at certain specified times, i.e., 120 minutes after the $C_8$ feed was injected (Example 25), 106 minutes (Example 26), 90 minutes (Example 27) and 85 minutes (Example 28); and the effluent compositions at the specified times were analyzed with the results shown in Table II.

TABLE II

| | Ex. 25 | Ex. 26 | Ex. 27 | Ex. 28 |
|---|---|---|---|---|
| Sieve | KY | KY | KY | KY |
| Weak Carrier-Eluent Composition, Wt. % | | | | |
| toluene | 5 | 10 | 15 | 20 |
| n-$C_{12}$ | 95 | 90 | 85 | 80 |
| Duration of Injection, Mins. | 90 | 80 | 75 | 65 |
| Strong Carrier-Eluent Composition, Wt. % | | | | |
| toluene | 60 | 60 | 60 | 60 |
| n-$C_{12}$ | 40 | 40 | 40 | 40 |
| Duration of Injection, Mins. | 60 | 60 | 60 | 60 |
| Time When the Effluent Sample was Taken, Mins. | 120 | 106 | 90 | 85 |
| Sample Composition Wt. % based on the total effluent at the specified time | | | | |
| p-xylene | 1.5 | 1.5 | 1.5 | 1.5 |
| m-xylene | 0.7 | 0.14 | 0.07 | <0.001 |
| o-xylene | 0.2 | 0.04 | 0.03 | <0.001 |
| ethylbenzene | 0.05 | 0.007 | 0.005 | <0.001 |

The above data indicates that, even with the employment of about 5 percent toluene in the weaker carrier-eluent mixture, a significant amount of contamination of the paraxylene product may take place at least at a relatively early stage of the desorption process.

What is claimed is:

1. In a process for continuously separating, in a liquid phase, the components of a liquid $C_8$ aromatic feedstream wherein at least one of said components is selectively adsorbed by contact with a solid sorbent material utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent material, wherein said continuous separation is achieved by:
    i. introducing a desorbent stream into the first section of said desorption zone;
    ii. withdrawing a desorption effluent comprising at least one selectively sorbed component from the last section of said desorption zone;
    iii. introducing said $C_8$ aromatic feedstream into the first section of said sorption zone; and
    iv. withdrawing a raffinate effluent comprising a less sorbed component from the last section of said sorption zone, the improvement which comprises:
    a. introducing a first desorbent stream comprising a desorbent material selected from the group consisting of toluene, m-diisopropylbenzene, p-diethylbenzene, o-dichlorobenzene and a mixture of diethylbenzene isomers in an amount ranging from about 40 to about 100 weight percent and an inert paraffinic material having from 8 to 16 carbon atoms in an amount ranging from 0 to 60 weight percent into the first section of said desorption zone; and b. introducing a second desorbent stream comprising said desorbent material in an amount ranging from about 10 to about 60 weight percent and said inert paraffinic material in an amount ranging from about 40 to about 90 weight percent into the first section of said rectification zone and wherein the concentration of said desorbent material present in the second desorbent stream is lower than the concentration of said desorbent material present in the first desorbent stream by at least 20 weight percent.

2. The process of claim 1 wherein the first desorbent stream is heated, before it is introduced into the first section of said desorption zone, to a temperature higher than the temperature of the second desorbent stream.

3. The process of claim 1 wherein said $C_8$ aromatic feed mixture comprises paraxylene and ethylbenzene.

4. The process of claim 3 wherein said selectively sorbed component withdrawn in step (ii) is paraxylene.

5. In a process for continuously separating, in a liquid phase, the components of a liquid $C_8$ aromatic feedstream comprising paraxylene and ethylbenzene wherein at least one of said components is selectively adsorbed by contact with a solid sorbent material utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent material, wherein said continuous separation is achieved by:

i. introducing a desorbent stream into the first section of said desorption zone;

ii. withdrawing a desorption effluent comprising at least one selectively sorbed component from the last section of said desorption zone;

iii. introducing said $C_8$ aromatic feedstream into the first section of said sorption zone; and iv. withdrawing a raffinate effluent comprising a less sorbed component from the last section of said sorption zone, the improvement which comprises:

a. introducing a first desorbent stream comprising a desorbent material selected from the group consisting of m-diisopropylbenzene, toluene, p-diethylbenzene, o-dichlorobenzene and a mixture of diethylbenzene isomers in an amount ranging from about 40 to about 100 weight percent and an inert paraffinic material having from 8 to 16 carbon atoms in an amount ranging from 0 to 60 weight percent into the first section of said desorption zone; and b. introducing a second desorbent stream comprising said desorbent material in an amount ranging from about 10 to about 60 weight percent and said inert paraffinic material in an amount ranging from about 40 to about 90 weight percent into the first section of said rectification zone and wherein the concentration of said desorbent material present in the second desorbent stream is lower than the concentration of said desorbent material present in the first desorbent stream by at least 20 weight percent.

6. The process of claim 5 wherein the first desorbent stream is heated, before it is introduced into the first section of said desorption zone, to a temperature higher than the temperature of the second desorbent stream.

7. The process of claim 5 wherein said selectively sorbed component withdrawn in step (ii) is paraxylene.

8. The process of claim 5 wherein said $C_8$ aromatic feed mixture comprises paraxylene, ethylbenzene, orthoxylene and metaxylene.

9. The process of claim 8 wherein said selectively sorbed components withdrawn in step (ii) are paraxylene and ethylbenzene.

10. The process of claim 5 wherein the first desorbent stream comprises said desorbent material in an amount ranging from about 50 to about 95 weight percent and said inert paraffinic material in an amount ranging from about 5 to about 50 weight percent.

11. The process of claim 5 wherein said solid sorbent material is a crystalline aluminosilicate selected from the group consisting of potassium substituted zeolite X, potassium substituted zeolite Y, barium substituted zeolite X, barium substituted zeolite Y, barium and potassium substituted zeolite X and barium and potassium substituted zeolite Y.

12. The process of claim 5 wherein said desorbent material is m-diisopropylbenzene.

13. The process of claim 5 wherein said desorbent material is toluene.

14. The process of claim 5 wherein said inert material is $n-C_{12}$ paraffin.

15. In a process for continuously separating, in a liquid phase, the components of a liquid $C_8$ aromatic feedstream wherein at least one of said components is selectively adsorbed by contact with a solid sorbent material utilizing a simulated countercurrent flow system wherein liquid streams are allowed to flow downward through a desorption zone, a rectification zone and a sorption zone, each zone being serially and circularly interconnected and divided into a plurality of serially interconnected sections, each section being packed with a mass of said solid sorbent material, wherein said continuous separation is achieved by:

i. introducing a desorbent stream into the first section of said desorption zone;

ii. withdrawing a desorption effluent comprising at least one selectively sorbed component from the last section of said desorption zone; iii. introducing said $C_8$ aromatic feed mixture into the first section of said sorption zone; and iv. withdrawing a raffinate effluent comprising a less sorbed component from the last section of said sorption zone;

the improvement which comprises:

a. heating a desorbent stream comprising a desorbent material selected from the group consisting of toluene, m-diisopropylbenzene, p-diethylbenzene, o-dichlorobenzene and a mixture of diethylbenzene isomers in an amount ranging from about 15 to about 100 weight percent and an inert paraffinic material having from 8 to 16 carbon atoms in an amount ranging from 0 to 85 weight percent to a temperature which is at least about 15° C. higher than the operating temperature of said rectification zone;

b. introducing said heated desorbent stream into the first section of said desorption zone;

c. cooling a portion of the desorption effluent withdrawn from the last section of said desorption zone to a temperature which is substantially identical to the operating temperature of said rectification zone; and, thereafter, d. introducing said cooled portion of the desorption effluent into the first section of said rectification zone.

16. The process of claim 15 wherein said $C_8$ aromatic feed mixture comprises paraxylene and ethylbenzene.

17. The process of claim 16 wherein said selectively sorbed component withdrawn in step (ii) is paraxylene.

18. The process of claim 15 wherein said $C_8$ aromatic feed mixture comprises paraxylene, ethylbenzene, orthoxylene and metaxylene.

19. The process of claim 18 wherein said desorption effluent withdrawn in step (ii) comprises paraxylene and ethylbenzene.

20. The process of claim 15 wherein the desorbent stream comprises said desorbent material in an amount ranging from about 20 to about 80 weight percent and said inert paraffinic material in an amount ranging from about 20 to about 80 weight percent.

21. The process of claim 20 wherein the desorbent stream comprises said desorbent material in an amount ranging from about 25 to about 67 weight percent and said inert paraffinic material in an amount ranging from about 33 to about 75 weight percent.

* * * * *